United States Patent
Boughorbel et al.

(10) Patent No.: US 10,128,080 B2
(45) Date of Patent: Nov. 13, 2018

(54) THREE-DIMENSIONAL IMAGING IN CHARGED-PARTICLE MICROSCOPY

(71) Applicant: FEI Company, Hillsboro, OR (US)

(72) Inventors: Faysal Boughorbel, Eindhoven (NL); Pavel Potocek, Eindhoven (NL); Ingo Gestmann, Duisburg (DE)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 15/413,216

(22) Filed: Jan. 23, 2017

(65) Prior Publication Data
US 2017/0309448 A1    Oct. 26, 2017

(30) Foreign Application Priority Data
Apr. 26, 2016   (EP) .................................... 16166998

(51) Int. Cl.
*H01J 37/28*     (2006.01)
*H01J 37/20*     (2006.01)
(Continued)

(52) U.S. Cl.
CPC ............ *H01J 37/28* (2013.01); *G01N 23/225* (2013.01); *H01J 37/20* (2013.01); *H01J 37/222* (2013.01);
(Continued)

(58) Field of Classification Search
CPC ............. G01N 2223/423; G01N 23/00; G01N 2223/401; G01N 2223/418; G01N 23/225;
(Continued)

(56) References Cited

U.S. PATENT DOCUMENTS

| | | | |
|---|---|---|---|
| 8,232,523 B2 * | 7/2012 | Boughorbel ......... | H01J 37/222 250/306 |
| 8,581,189 B2 * | 11/2013 | Boughorbel ......... | H01J 37/222 250/306 |

(Continued)

OTHER PUBLICATIONS

"Electron Microscope", Wikipedia, Retrieved from the Internet Oct. 15, 2015, http://en.wikipedia.org/wiki/Electron_microscope, 11 pages.

(Continued)

*Primary Examiner* — Wyatt Stoffa
(74) *Attorney, Agent, or Firm* — Scheinberg & Associates, P.C.; Michael O. Scheinberg

(57) ABSTRACT

A method of investigating a specimen using charged-particle microscopy, and a charged particle microscope configured for same. In one embodiment, the method includes: (a) selecting a virtual sampling grid on a surface of a specimen, the virtual sampling grid extending in an XY plane and comprising nodes to be impinged upon by a beam of charged particles; (b) selecting a landing energy for the beam, the landing energy associated with a penetration depth; (c) generating a scan image by irradiating the specimen at each of the nodes with the beam, and detecting output radiation emanating from the specimen in response thereto; (d) repeating steps (b) and (c) for a series of different landing energies corresponding to an associated series of penetration depths, (e) pre-selecting an energy increment by which the landing energy is to be altered after a first iteration of steps (b) and (c); (f) associating the energy increment with a corresponding depth increment; (g) selecting the virtual sampling grid to have a substantially equal node pitch p in X and Y, which pitch p is matched to the value of the depth increment so as to produce a substantially cubic sampling voxel; and (h) selecting subsequent energy values in the series of landing energies so as to maintain a substantially constant depth (Continued)

Figure 1:
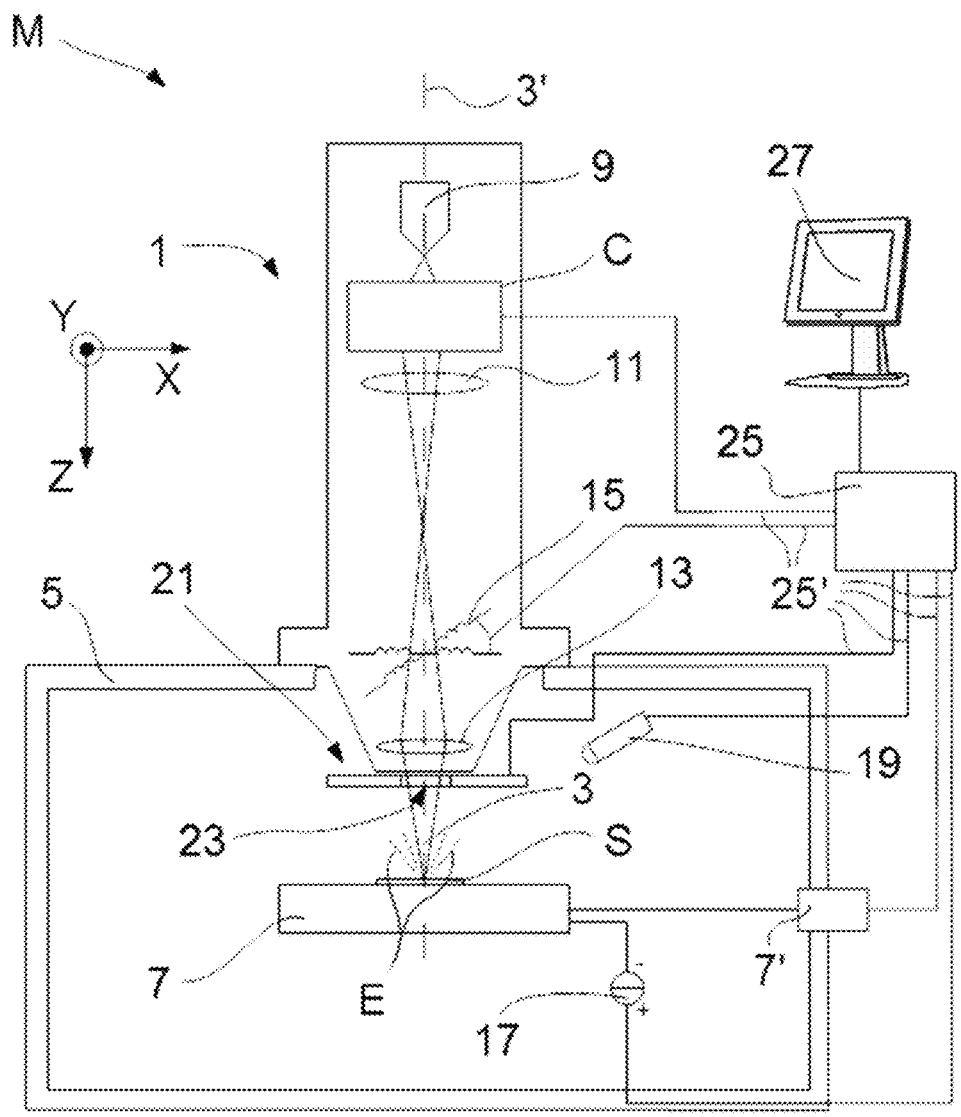

increment between consecutive members of the series of penetration depths.

20 Claims, 3 Drawing Sheets

(51) Int. Cl.
*H01J 37/244* (2006.01)
*H01J 37/22* (2006.01)
*G01N 23/225* (2018.01)

(52) U.S. Cl.
CPC ...... *H01J 37/244* (2013.01); *G01N 2223/079* (2013.01); *G01N 2223/08* (2013.01); *G01N 2223/423* (2013.01); *H01J 2237/226* (2013.01)

(58) Field of Classification Search
CPC .. G01N 23/22; H01J 2237/226; H01J 37/222; H01J 37/28; H01J 2237/221; H01J 2237/2803; H01J 2237/2809
See application file for complete search history.

(56) References Cited

U.S. PATENT DOCUMENTS

| | | | | |
|---|---|---|---|---|
| 8,586,921 | B2* | 11/2013 | Boughorbel | H01J 37/222 250/306 |
| 8,704,176 | B2* | 4/2014 | Boughorbel | G01N 23/225 250/306 |
| 2004/0046125 | A1* | 3/2004 | Chen | H01J 37/141 250/396 ML |
| 2011/0266440 | A1* | 11/2011 | Boughorbel | H01J 37/222 250/310 |
| 2013/0037714 | A1* | 2/2013 | Boughorbel | H01J 37/222 250/307 |
| 2013/0037715 | A1* | 2/2013 | Boughorbel | H01J 37/222 250/307 |
| 2013/0228683 | A1 | 9/2013 | Boughorbel et al. | |
| 2014/0312226 | A1* | 10/2014 | Boughorbel | G01N 23/225 250/307 |
| 2015/0371815 | A1* | 12/2015 | Potocek | G02B 21/0048 250/307 |
| 2016/0013015 | A1* | 1/2016 | Potocek | G02B 21/002 250/307 |
| 2017/0162363 | A1* | 6/2017 | Kim | H01J 37/222 |

OTHER PUBLICATIONS

"Focused Ion Beam", Wikipedia, Retrieved from the Internet Jul. 11, 2016, https://en.wikipedia.org/wiki/Focused_ion_beam, 7 pages.

"Scanning Electron Microscope", Wikipedia. Retrieved from the Internet Jul. 25, 2016, http://en.wikipedia.org/wiki/Scanning_electron_microscope, 23 pages.

"Scanning Helium Ion Microscope", Wikipedia, Retrieved from the Internet on Jul. 25, 2016, http://en.wikipedia.org/wiki/Scanning_Helium_Ion_Microscope, 2 pages.

"Scanning Transmission Electron Microscopy", Wikipedia, Retrieved from the Internet Jul. 25, 2016, http://en.wikipedia.org/wiki/Scanning_transmission_electron_microscopy, 5 pages.

"Transmission Electron Microscopy", Wikipedia, Retrieved from the Internet Jul. 25, 2016, http://en.wikipedia.org/wiki/Transmission_electron_microscopy, 23 pages.

Escovitz, W.H. et al., "Scanning Transmission Ion Microscope with a Field Ion Source," Proc. Nat. Acad. Sci. USA, May 1975, pp. 1826-1828, vol. 72, No. 5.

Giannuzzi, Lucille A., "Dose accumulation and 3D imaging with He+ ions," J. Vac Sci. Technol. B, vol. 33, No. 1, Jan./Feb. 2015, 6 pages.

Varentsov, D. et al. "First biological images with high-energy proton microscopy", Physica Medica (2013), pp. 208-213, vol. 29.

* cited by examiner

THREE-DIMENSIONAL IMAGING IN CHARGED-PARTICLE MICROSCOPY

The invention relates to a method of investigating a specimen using charged-particle microscopy, comprising the following steps:
  (a) On a surface of the specimen, selecting a virtual sampling grid extending in an XY plane and comprising grid nodes to be impinged upon by a charged-particle probing beam during a two-dimensional scan of said surface;
  (b) Selecting a landing energy $E_i$ for said probing beam, with an associated nominal Z penetration depth $d_i$ below said surface;
  (c) At each of said nodes, irradiating the specimen with said probing beam and detecting output radiation emanating from the specimen in response thereto, thereby generating a scan image $I_i$;
  (d) Repeating steps (b) and (c) for a series $\{E_i\}$ of different landing energies, corresponding to an associated series $\{d_i\}$ of different penetration depths.
Here, directions XYZ are associated with a selected Cartesian coordinate system.

The invention also relates to a Charged Particle Microscope, comprising:
  A specimen holder, for holding a specimen;
  A source, for producing a probing beam of charged particles;
  An illuminator, for directing said beam so as to irradiate the specimen;
  A detector, for detecting a flux of output radiation emanating from the specimen in response to said irradiation,
further comprising a processor that is configured to perform such a method.

Charged particle microscopy is a well-known and increasingly important technique for imaging microscopic objects, particularly in the form of electron microscopy. Historically, the basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" Focused Ion Beam (FIB), allowing supportive activities such as ion-beam milling or Ion-Beam-Induced Deposition (IBID), for example. More specifically:
  In a SEM, irradiation of a specimen by a scanning electron beam precipitates emanation of "auxiliary" output radiation from the specimen, in the form of secondary electrons, backscattered electrons, X-rays and photoluminescence (infrared, visible and/or ultraviolet photons), for example; one or more components of this output radiation is/are then detected and used for image accumulation purposes.
  In a TEM, the electron beam used to irradiate the specimen is chosen to be of a high-enough energy to penetrate the specimen (which, to this end, will generally be thinner than in the case of a SEM specimen); the transmitted electrons emanating from the specimen can then be used to create an image. When such a TEM is operated in scanning mode (thus becoming a STEM), the image in question will be accumulated during a scanning motion of the irradiating electron beam.
More information on some of the topics elucidated here can, for example, be gleaned from the following Wikipedia links:
  en.wikipedia.org/wiki/Electron_microscope
  en.wikipedia.org/wiki/Scanning_electron_microscope
  en.wikipedia.org/wiki/Transmission_electron_microscopy
  en.wikipedia.org/wiki/Scanning_transmission_electron_microscopy
As an alternative to the use of electrons as irradiating beam, charged particle microscopy can also be performed using other species of charged particle. In this respect, the phrase "charged particle" should be broadly interpreted as encompassing electrons, positive ions (e.g. Ga or He ions), negative ions, protons and positrons, for instance. As regards non-electron-based charged particle microscopy, some further information can, for example, be gleaned from references such as the following:
  en.wikipedia.org/wiki/Focused_ion_beam
  en.wikipedia.org/wiki/Scanning_Helium_Ion_Microscope
  W. H. Escovitz, T. R. Fox and R. Levi-Setti, *Scanning Transmission Ion Microscope with a Field Ion Source*, Proc. Nat. Acad. Sci. USA 72(5), pp 1826-1828 (1975). www.ncbi.nlm.nih.gov/pubmed/22472444
It should be noted that, in addition to imaging and performing (localized) surface modification (e.g. milling, etching, deposition, etc.), a charged particle microscope may also have other functionalities, such as performing spectroscopy, examining diffractograms, etc.

In all cases, a Charged Particle Microscope (CPM) will comprise at least the following components:
  A radiation source, such as a Schottky electron source or ion gun.
  An illuminator, which serves to manipulate a "raw" radiation beam from the source and perform upon it certain operations such as focusing, aberration mitigation, cropping (with an aperture), filtering, etc. It will generally comprise one or more (charged-particle) lenses, and may comprise other types of (particle-) optical component also. If desired, the illuminator can be provided with a deflector system that can be invoked to cause its exit beam to perform a scanning motion across the specimen being investigated.
  A specimen holder, on which a specimen under investigation can be held and positioned (e.g. tilted, rotated). If desired, this holder can be moved so as to effect scanning motion of the beam w.r.t. the specimen. In general, such a specimen holder will be connected to a positioning system such as a mechanical stage.
  A detector (for detecting output radiation emanating from an irradiated specimen), which may be unitary or compound/distributed in nature, and which can take many different forms, depending on the output radiation being detected. Examples include photodiodes, CMOS detectors, CCD detectors, photovoltaic cells, X-ray detectors (such as Silicon Drift Detectors and Si(Li) detectors), etc. In general, a CPM may comprise several different types of detector, selections of which can be invoked in different situations.
  A processor (electronic controller), inter alia for administrating/controlling certain operations within the CPM, executing software/firmware, performing autonomous runs, exchanging data with a user interface, etc.
In the case of a transmission-type microscope (such as a (S)TEM, for example), the CPM will also comprise:
  An imaging system, which essentially takes charged particles that are transmitted through a specimen (plane) and directs (focuses) them onto analysis apparatus, such as a detection/imaging device, spectroscopic apparatus (such as an EELS device), etc. As with the illuminator referred to above, the imaging system may also perform other functions, such as aberration mitigation, cropping, filtering, etc., and it will generally comprise one or more charged-particle lenses and/or other types of particle-optical components.

In what follows, the invention may—by way of example—sometimes be set forth in the specific context of electron microscopy; however, such simplification is intended solely for clarity/illustrative purposes, and should not be interpreted as limiting.

A method as set forth in the opening paragraph above is, for example, known in various forms from U.S. Pat. No. 8,232,523 and U.S. Pat. No. 8,581,189 (incorporated herein by reference), which have an inventor in common with the present invention. Said patents describe multi-energy data acquisition schemes in which:

A set of "raw" SEM images is acquired at different landing energies;

These raw images are used as input to a mathematical deconvolution algorithm, which "disentangles" them and produces a three-dimensional, depth-resolved "super-image".

Although said patents have produced a revolution in three-dimensional imaging, they have an attendant computational overhead due to the non-trivial mathematical deconvolution procedures that are required to produce an ultimate depth-resolved image. The current inventors have set themselves the goal of providing an alternative approach.

It is an object of the invention to provide an alternative three-dimensional imaging technique for use in a CPM. In particular, it is an object of the invention that this novel technique should involve less computational overhead than prior-art techniques.

These and other objects are achieved in a method as set forth in the opening paragraph above, characterized by the following steps:

(e) Pre-selecting an initial energy increment $\Delta E_i$ by which $E_i$ is to be altered after a first iteration of steps (b) and (c);

(f) Associating energy increment $\Delta E_i$ with a corresponding depth increment $\Delta d$ in the value of $d_i$;

(g) Selecting said sampling grid to have a substantially equal node pitch p in X and Y, which pitch p is matched to the value of $\Delta d$ so as to produce a substantially cubic sampling voxel;

(h) Selecting subsequent energy values in the series $\{E_i\}$ so as to maintain a substantially constant depth increment $\Delta d$ between consecutive members of the series $\{d_i\}$, within the bounds of selected minimum and maximum landing energies $E_{min}$ and $E_{max}$, respectively.

In the context of the invention as here presented, the following considerations deserve mention:

The initial energy increment $\Delta E_i$ (and thereby the associated depth increment $\Delta d$) can essentially be freely chosen, although, in practice, factors such as desired throughput, detector sensitivity, desired resolution, etc., will tend to place upper/lower limits on $\Delta E_i$ (and thus $\Delta d$) in a given situation (see below).

The minimum landing energy $E_{min}$ can essentially be freely chosen. However, there will often be a practical lower limit on $E_{min}$ in a given situation, e.g. associated with a minimum acceptable detector Contrast-to-Noise Ratio (CNR) [the energy of the output radiation (e.g. backscattered electrons) emanating from the specimen in response to irradiation by the probing beam will have an energy≤the employed landing energy].

The maximum landing energy $E_{max}$ can essentially be freely chosen. However, there will often be a practical upper limit on $E_{max}$ in a given situation, e.g. associated with a desired cumulative radiation dose for the specimen (see below).

Figure 3:
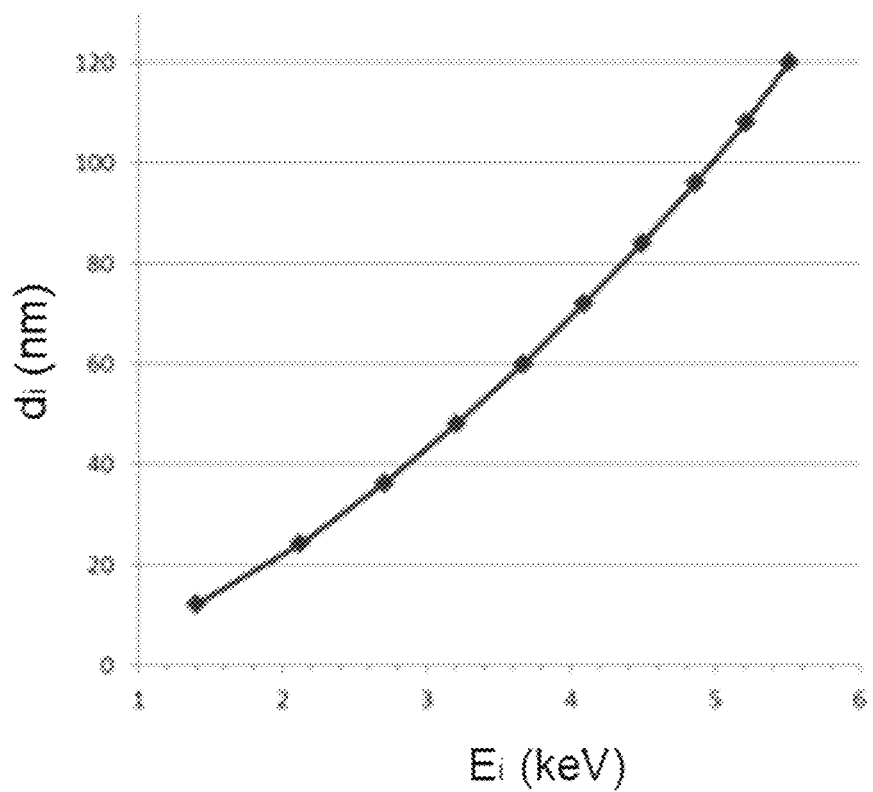

The relationship between the probing beam's landing energy $E_i$ and its associated nominal Z penetration depth $d_i$ is typically a power law of the form:

$$d_i \sim k E_i^a$$

in which the values of scaling factor k and power a depend inter alia on the material of the specimen and the species of probing charged particle being used (see FIG. 3, for example). In many practical cases, this power law will essentially take the form of a (quasi-)linear relationship:

$$d_i \sim k E_i$$

With due regard to the previous item, one can, for example, choose appropriate values in the energy series $\{E_i\}$—so as to achieve substantially equal depth increments $\Delta d$ in the set $\{d_i\}$—on the basis of one or more of the following:

A physical model that uses a (specific) functional relationship between $d_i$ and $E_i$, allowing values of the members of $\{E_i\}$ to be calculated;

A prior calibration, in which one empirically determines an (approximate) relationship between $E_i$ and $d_i$, whereby, in either/both instances, use may, for example, be made of (a certain amount of) extrapolation/interpolation and/or averaging.

The skilled artisan will be able to select/determine values of these various parameters/variables that suit the particulars of a given situation, such as specimen type, species of charged particle in the probing beam, detected species of output radiation emanating from the specimen, etc.

The invention exploits the novel insight that, if multi-energy data acquisition is done in a certain manner, then one can perform particle-optical depth-sectioning of a specimen without the need to mathematically deconvolve the acquired series of scan images. When a probing beam of charged particles impinges on a specimen surface, it produces a sub-surface Point Spread Function (PSF) that describes the manner in which the initial beam "diffuses through" (interacts with) the sample bulk; this PSF is often somewhat "tear-shaped" or quasi-conical in form, with an apex at the specimen surface that widens out as one progresses downward into the specimen. Associated with the PSF is an intensity curve that is essentially bell-shaped, with a high central peak and peripheral flanks that taper off on each side. Because the probing beam impinges upon the specimen surface at successive points in a matrix-like/net pattern—produced by sampling at the nodes of the employed sampling grid—a corresponding (two-dimensional) array of sub-surface PSFs is generated during a sampling run. Depending on the distance between sampling nodes, neighboring PSFs will mutually overlap to a greater or lesser extent, and the flanks of their associated intensity curves will also overlap to a corresponding extent—a phenomenon that will here be referred to as "crosstalk" (see FIG. 2, for example). The inventors have arrived at the insight that such crosstalk lies at the root of the above-mentioned deconvolution task and that, if the crosstalk can be suitably minimized/optimized, a follow-on deconvolution procedure is essentially obviated. In this regard, the inventors discovered that it was advantageous to:

Radiatively "drill" the specimen in successive depth steps of size $\Delta d$;

Use a sampling grid with substantially square cells of side length (node pitch) $p \sim \Delta d$, resulting in an essentially cubic sampling voxel for the various measurement sessions (steps). In so doing, one effectively equalizes the sampling resolution in X, Y and Z. Importantly, one pinches the above-mentioned intensity curves with respect to one another—making them less obtuse/more steep-flanked—thereby reducing/minimizing the relative overlapping of flanks from neighboring curves; this reduction in crosstalk substantially reduces blur, which would otherwise have to be computationally removed in a deconvolution procedure. This can be further understood by making an analogy to the so-called Rayleigh resolution criterion, in which attainable resolution is improved when the "spot size" (angular extent) of a probing beam is decreased. This innovative situation is best satisfied in a substantially isotropic sample.

It is worth noting that, if one deviates substantially from the sampling voxel cubicity advocated by the present invention, the following effects can be expected:

If the X/Y dimensions of the sampling voxels are substantially greater than their Z-dimension $\Delta d$ ("squat" or "flattened" cubes [tiles]), then there will tend to be a substantial loss of lateral resolution (overly coarse sampling).

If the X/Y dimensions of the sampling voxels are substantially smaller than their Z-dimension $\Delta d$ ("tall" or "stretched" cubes [pillars]), then this will tend to lead to suppression/destruction of higher frequencies in the associated Fourier spectrum.

In each case, some form of post-acquisition mathematical processing (deconvolution) will be required to try to correct for the effects of missing image information.

In a particular embodiment of the invention, after completion of step (h)/(d), a physical slicing process is used to remove from original surface $S_i$ a layer of material of nominal thickness L, thereby exposing a new surface $S_m$. Examples of physical slicing processes that can be used in this context include microtoming, milling, etching (including chemical etching), ablation, etc., whereby the adjective "physical" as here employed is intended to distinguish from "radiative" depth-sectioning. The essence of this embodiment is the realization that there is generally a practical limit to $E_{max}$ in that, if one attempts to radiatively depth-section the specimen to too great a depth, this will typically entail too great a radiation dose for the overlying specimen material—which may damage the specimen, and change its behavior vis-à-vis the charged particle beam pervading it. To prevent this, one can instead perform radiative depth-sectioning to a "safe" level $d_{max}$, followed by physical material removal so as to expose a fresh surface $S_m$. In this regard, an advantageous scenario is one in which:

A maximum penetration depth $d_{max}$ is associated with $E_{max}$;

$L \leq d_{max}$;

Steps (a)-(h) are repeated on said new surface $S_m$, which procedure may, if desired, be repeated again in several iterations. Theoretically, one could consider $L = d_{max}$ to be an ideal scenario, but this may be practically unattainable, due (for example) to surface roughness effects and positioning inaccuracy. To err on the safe side, one may instead choose a value of L that is a little less than $d_{max}$ (e.g. by 5-10%), so as to avoid over-removal of material. The skilled artisan will be able to choose values of $E_{max}/d_{max}$ and L that suit the needs and particulars of a given situation, such as the employed specimen type, its previous irradiation history, throughput considerations, etc.

As regards the employed maximum landing energy $E_{max}$, this may, for example, be chosen to lie in the range:

5-8 keV, for specimens comprising biological tissue (usually aqueous in nature);

30-60 keV, for specimens that are substantially non-biological (such as mineralogical/petrological, metallurgic, crystallographic and/or semiconductor specimens, etc.).

Considerations to be borne in mind when choosing $E_{max}$ include the following:

An upper bound on $E_{max}$ will (inter alia) be determined by the cumulative radiation dose that can be withstood by the (irradiated upper layers of the) specimen.

Using a sub-optimally small value of $E_{max}$ will effectively under-utilize the invention, and increase the relative weight of physical slicing to radiative slicing.

As regards the value of $\Delta d$, this may, for example, be selected to lie in the range 1-10 nm. One is essentially free to choose a value of $\Delta d$ according to desire, but one should nevertheless take stock of the following considerations:

If $\Delta d$ is sub-optimally small, then a throughput penalty will be incurred, since the number of depth increments/measurement sessions required to reach $d_{max}$ will increase. Similarly, if $\Delta d$—or, more particularly, the associated energy increment(s) $\Delta E_i$—is too small, it may clash with the ability of the employed detector to unambiguously register a difference between successive measurement sessions (inter alia due to noise effects). Moreover, a small $\Delta d$ will tend to increase crosstalk between neighboring depth-sections.

If $\Delta d$ is sub-optimally large, then it may overly coarsen the attainable imaging resolution. On the other hand, a relatively large value of $\Delta d$ (and associated energy increment(s) $\Delta E_i$) will tend to increase the prominence of the abovementioned intensity peak relative to background signal levels.

To give some non-binding guidance regarding the subject-matter of the previous two paragraphs, the following examples may be noted:

For bulk biological specimens, $E_i$ values in the range 0.5-5.0 keV will typically tend to produce $d_i$ values in a range of ca. 5-150 nm, respectively.

For thin-section biological specimens (e.g. with a thickness in the range 20-300 nm), an $E_{max}$ value of 7 keV will typically tend to produce a $d_{max}$ value of ca. 300 nm.

For silicon specimens, an $E_i$ value of 25 keV can typically be used to achieve a $d_i$ value of ca. 2 μm (BSE detection).

For Cu/metal structures in a Si substrate, an $E_i$ value of 25 keV can typically be used to achieve a $d_i$ value of ca. 500 nm (BSE detection).

For an Al sample in which Cu particles are embedded, an $E_i$ value of 20 keV can typically be used to achieve a $d_i$ value of ca. 500 nm.

The invention tends to produce its very best results (without having to resort to deconvolution) for relatively curtailed values of $d_{max}$, e.g. ca. 60 nm for typical biological specimens. Less-curtailed values (greater ultimate penetration depths) are still possible, though the quality of the results may then start to show some degree of deterioration for larger values of $d_i$ (approaching $d_{max}$). The skilled artisan will be able to decide for himself what value of $d_{max}$ to use, with an eye to achieving a given imaging quality.

In a particular embodiment of the invention, for each successive landing energy in said series $\{E_i\}$, the output radiation emanating from the specimen is selectively detected in at least one of the following manners:

By detecting only a given energy range $\Delta\varepsilon^i$ of the total energy spectrum of said output radiation, where $\Delta\varepsilon^i$ depends on $E_i$ (energy-filtered detection);

By detecting only a given angular range $\Delta\theta^i$ of the total angular spectrum of said output radiation, where $\Delta\theta^i$ depends on $E_i$ (angle-filtered detection).

Performing filtered detection in this manner provides a way of concentrating on output energy emission from a particular depth level in the specimen; in this way, concurrent signals from other depth levels in the sample are compressed, thus reducing degeneracy in the detected signal. A particular (optimized) choice of $\Delta\varepsilon^i$ and/or $\Delta\theta^i$ for each $E_i$ can, for example, be determined from:

A prior calibration run; and/or

A model describing the emission of output radiation by the specimen.

See, for example, in this regard, U.S. Pat. No. 8,704,176 and U.S. Pat. No. 8,586,921 (incorporated herein by reference), which have an inventor in common with the present invention, and which respectively describe how angular filtering/energy filtering of the energy emanating from an irradiated specimen can be used to "zoom in" on a particular sub-surface depth level—although one still captures information from other depth levels, thus requiring a mathematical deconvolution procedure to disentangle the various layer contributions (unlike the present invention).

It should be explicitly noted that the sub-surface depth increments that are stepped-through in the present invention may run in a direction that is "top-down" (increasing penetration) or "bottom-up" (decreasing penetration), according to choice. It should also be noted that, in a top-down approach, the first employed value of $E_i$ (or, similarly, the last employed $E_i$ value in a bottom-up approach) may produce a penetration depth $d_i$ that is less than $\Delta d$.

The invention will now be elucidated in more detail on the basis of exemplary embodiments and the accompanying schematic drawings, in which:

FIG. 1 renders a longitudinal cross-sectional view of a CPM in which the present invention is implemented.

Figure 2:
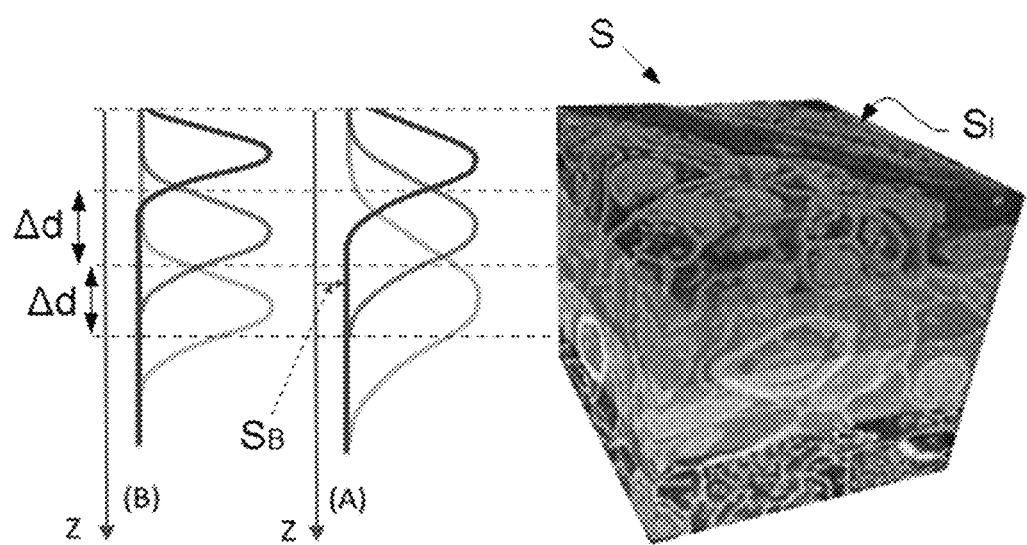

FIG. 2 renders an illustration of a principle underlying an embodiment of the present invention.

FIG. 3 shows an example of a functional relationship between landing energy and penetration depth in an embodiment of the present invention.

In the Figures, where pertinent, corresponding parts may be indicated using corresponding reference symbols.

EMBODIMENT 1

FIG. 1 is a highly schematic depiction of an embodiment of a CPM in which the present invention is implemented; more specifically, it shows an embodiment of a microscope M, which, in this case, is a SEM (though, in the context of the current invention, it could just as validly be a (S)TEM, or an ion-based microscope, for example). The microscope M comprises an illuminator (particle-optical column) 1, which produces a probing beam 3 of input charged particles (in this case, an electron beam) that propagates along a particle-optical axis 3'. The illuminator 1 is mounted on a vacuum chamber 5, which comprises a specimen holder 7 and associated stage/actuator 7' for holding/positioning a specimen S. The vacuum chamber 5 is evacuated using vacuum pumps (not depicted). With the aid of voltage supply 17, the specimen holder 7, or at least the specimen S, may, if desired, be biased (floated) to an electrical potential with respect to ground.

The illuminator 1 (in the present case) comprises an electron source 9 (such as a Schottky gun, for example), lenses 11, 13 to focus the electron beam 3 onto the specimen S, and a deflection unit 15 (to perform beam steering/scanning of the beam 3). The apparatus M further comprises a controller/computer processing apparatus 25 for controlling inter alia the deflection unit 15, lenses 11, 13 and detectors 19, 21, and displaying information gathered from the detectors 19, 21 on a display unit 27.

The detectors 19, 21 are chosen from a variety of possible detector types that can be used to examine different types of output radiation E emanating from the specimen S in response to irradiation by the input beam 3. In the apparatus depicted here, the following (non-limiting) detector choices have been made:

Detector 19 is a solid state detector (such as a photodiode) that is used to detect photoluminescence emanating from the specimen S. It could alternatively be an X-ray detector—such as Silicon Drift Detector (SDD) or Silicon Lithium (Si(Li)) detector—or an electron sensor (e.g. a (silicon/evacuated) photomultiplier), for instance. It may, if desired, be movable (e.g. so as to allow it to capture specific angular ranges of the flux E), and/or provided with an energy filter (e.g. so as to allow it to examine specific energy ranges of the flux E).

Detector 21 is a segmented silicon electron detector, comprising a plurality of independent detection segments (e.g. quadrants) disposed in annular configuration about a central aperture 23 (allowing passage of the primary beam 3). Such a detector can, for example, be used to investigate the angular dependence of a flux of output backscattered electrons emanating from the specimen S. It will typically be biased to a positive potential, so as to attract electrons emitted from the specimen S.

The skilled artisan will understand that many different types of detector can be chosen in a set-up such as that depicted.

By scanning the input beam 3 over the specimen S, output radiation—comprising, for example, X-rays, infrared/visible/ultraviolet light, secondary electrons (SEs) and/or backscattered electrons (BSEs)—emanates from the specimen S. Since such output radiation is position-sensitive (due to said scanning motion), the information obtained from the detectors 19, 21 will also be position-dependent. This fact allows (for instance) the signal from detector 21 to be used to produce a BSE image of (part of) the specimen S, which image is basically a map of said signal as a function of scan-path position on the specimen S.

The signals from the detectors 19, 21 pass along control lines (buses) 25', are processed by the controller 25, and can be displayed on display unit 27. Such processing may include operations such as combining, integrating, subtracting, false colouring, edge enhancing, and other processing known to the skilled artisan. In addition, automated recognition processes (e.g. as used for particle analysis) may be included in such processing.

It should be noted that many refinements and alternatives of such a set-up will be known to the skilled artisan, including, but not limited to:

The use of dual beams—for example an electron beam 3 for imaging and an ion beam for machining (or, in some cases, imaging) the specimen S;

The use of a controlled environment at the specimen S—for example, maintaining a pressure of several mbar (as used in a so-called Environmental SEM) or by admitting gases, such as etching or precursor gases, etc.

In the specific context of the current invention, the illuminator 1/electron source 9 can be adjusted so as to alter the landing energy $E_i$ of the probing beam 3; more specifically, $E_i$ can be increased (or decreased) incrementally so as to cause the beam 3 to penetrate to successively greater (or lesser) depths $d_i$ in the specimen S. Making use of a known relationship $d_i = f(E_i)$ between $E_i$ and $d_i$ (see Embodiment 3, for example), one can (pre-)select a series $\{E_i\}$ of incrementally altered energy values in such a way that the associated series $\{d_i\}$ of incrementally altered depth values has successive members that mutually differ by a substantially constant depth increment $\Delta d$—thereby ensuring that successive sub-surface levels/bands probed by the beam 3 are substantially equally spaced in Z. Moreover, one can pre-match the X/Y dimensions of a scan grid on a presented surface of the specimen S such that a (repeating) cell of said grid is substantially square with a side length substantially equal to $\Delta d$; this scan grid is then used by controller 25 to execute an XY (e.g. serpentine, raster or spiral) scanning motion of beam 3 relative to specimen S, e.g. by sending appropriate setpoints to stage 7' or/and deflector 15'.

It should be noted that actions such as determining the relationship $d_i = f(E_i)$ [or performing an equivalent calibration], determining $\{E_i\}$, etc., can be performed fully automatically (e.g. with the aid of software/firmware executed by controller 25), or fully manually, or using a hybrid automatic/manual approach, as desired.

EMBODIMENT 2

FIG. 2 renders a schematic illustration of a principle underlying the present invention. The Figure graphically depicts sub-surface intensity curves for probing beams of successively increasing (or decreasing) landing energy that impinge on a presented surface $S_i$ of specimen S, whereby:

The curves in portion (A) correspond to a prior-art approach;

The curves in portion (B) correspond to an embodiment of the current invention.

Note that individual curves are essentially bell-shaped, and are here depicted after subtraction of a background signal level $S_B$. In particular, note that, as compared to the prior-art curves (A), the curves in portion (B) are sharper, with a more Z-confined peak and steeper flanks. As a result, the point of overlap of the "shoulders" of neighboring curves in portion (B) is further down from the peak than in case (A), resulting in crosstalk reduction as set forth above. An Airy disk associated with curves (B) is also more confined than for curves (A).

EMBODIMENT 3

This embodiment presents a possible manner in which to determine a functional relationship $d_i = f(E_i)$ using a calibration routine, whereby use is made of a combination of physical cutting and multi-energy (ME) radiative slicing to analyze BSE information depth. It should be noted that localized information corresponds mainly to the peak position in an emission layer, although the total BSE signal is spread across a wider range. A possible embodiment of this calibration involves alternating ME BSE imaging with serial physical cutting of the same volume. To obtain an optimally accurate calibration, both physical and ME radiative slicing are ideally performed with the highest resolution possible (smallest depth steps). After a sufficiently large dataset is obtained, subsurface ME images are matched to the most similar ones in the physical slicing dataset—whereby similarity can, for example, be assessed based on mathematical measures such as the Sum of Squared Differences (SSD), Sum of Absolute Differences (SAD), or Structural Similarity Index (SSI) metrics, for instance. Given that each layer in the physical slices stack is associated with a known depth value, this comparison will lead to a depth-of-information curve that interrelates landing energy and detected BSE depth. FIG. 3 shows an example of such a curve.

The invention claimed is:

1. A method of investigating a specimen using charged-particle microscopy, comprising:
    (a) on a surface of the specimen, selecting a virtual sampling grid extending in an XY plane and having grid nodes to be impinged upon by a charged-particle probing beam during a two-dimensional scan of said surface;
    (b) selecting a landing energy $E_i$ for said charged-particle probing beam, with an associated nominal Z penetration depth $d_i$ below said surface;
    (c) at each of said grid nodes, irradiating the specimen with said charged-particle robing beam and detecting output radiation emanating from the specimen in response thereto, thereby generating a scan image $I_i$;
    (d) repeating steps (b) and (c) for a series $\{E_i\}$ of different landing energies, corresponding to an associated series $\{d_i\}$ of different penetration depths;
    (e) pre-selecting an initial energy increment $\Delta E_i$ by which $E_i$ is to be altered after a first iteration of steps (b) and (c);
    (f) associating energy increment $\Delta E_i$ with a corresponding depth increment $\Delta d$ in the value of $d_i$;
    (g) selecting said virtual sampling grid to have a substantially equal node pitch p in X and Y, which pitch p is matched to the value of $\Delta d$ so as to produce a substantially cubic sampling voxel; and
    (h) selecting subsequent energy values in the series $\{E_i\}$ so as to maintain a substantially constant depth increment $\Delta d$ between consecutive members of the series $\{d_i\}$.

2. A method according to claim 1, wherein, after completion of step (h), a physical slicing process is used to remove from said surface a layer of material of nominal thickness L, thereby exposing a new surface.

3. A method according to claim 2, wherein:
    the series $\{E_i\}$ comprises a maximum landing energy $E_{max}$;
    a maximum penetration depth $d_{max}$ is associated with $E_{max}$;
    $L \leq d_{max}$; and
    steps (a)-(h) are repeated on said new surface.

4. A method according to claim 1, wherein, in step (h), values of $E_i$ in the series $\{E_i\}$ are selected using at least one of:
    a functional relationship between $E_i$ and $d_i$ derived from a physical model; and
    at least one of extrapolation, interpolation and averaging, carried out with respect to an empirical relationship between $E_i$ and $d_i$ that is derived from a prior calibration.

5. A method according to claim 1, wherein, for each successive landing energy in said series $\{E_i\}$, said output radiation emanating from the specimen is selectively detected in at least one of the following manners:

by detecting only a given energy range $\Delta\varepsilon^i$ of the total energy spectrum of said output radiation, where $\Delta\varepsilon^i$ depends on $E_i$; and by detecting only a given angular range $\Delta\theta^i$ of the total angular spectrum of said output radiation, where $\Delta\theta^i$ depends on $E_i$.

6. A method according to claim 1, wherein the series $\{E_i\}$ comprises a maximum landing energy $E_{max}$, and wherein:

the sample comprises biological tissue and $E_{max}$ is in a range of from 5 keV to 8 keV; or the sample is substantially non-biological and $E_{max}$ is in a range of from 30 keV to 60 keV.

7. A method according to claim 1, wherein $\Delta d$ is in a range of from 1 nm to 10 nm.

8. A method according to claim 1, wherein a series of scan images resulting from step (d) is not subjected to a mathematical deconvolution procedure.

9. A method according to claim 2, wherein, in step (h), values of $E_i$ in the series $\{E_i\}$ are selected using at least one of:

a functional relationship between $E_i$ and $d_i$ derived from a physical model; and at least one of extrapolation, interpolation and averaging, carried out with respect to an empirical relationship between $E_i$ and $d_i$ that is derived from a prior calibration.

10. A method according to claim 3, wherein, in step (h), values of $E_i$ in the series $\{E_i\}$ are selected using at least one of:

a functional relationship between $E_i$ and $d_i$ derived from a physical model; and at least one of extrapolation, interpolation and averaging, carried out with respect to an empirical relationship between $E_i$ and $d_i$ that is derived from a prior calibration.

11. A method according to claim 2, wherein, for each successive landing energy in said series $\{E_i\}$, said output radiation emanating from the specimen is selectively detected in at least one of the following manners:

by detecting only a given energy range $\Delta\varepsilon^i$ of the total energy spectrum of said output radiation, where $\Delta\varepsilon^i$ depends on $E_i$; and by detecting only a given angular range $\Delta\theta^i$ of the total angular spectrum of said output radiation, where $\Delta\theta^i$ depends on $E_i$.

12. A method according to claim 3, wherein, for each successive landing energy in said series $\{E_i\}$, said output radiation emanating from the specimen is selectively detected in at least one of the following manners:

by detecting only a given energy range $\Delta\varepsilon^i$ of the total energy spectrum of said output radiation, where $\Delta\varepsilon^i$ depends on $E_i$; and by detecting only a given angular range $\Delta\theta^i$ of the total angular spectrum of said output radiation, where $\Delta\theta^i$ depends on $E_i$.

13. A method according to claim 4, wherein, for each successive landing energy in said series $\{E_i\}$, said output radiation emanating from the specimen is selectively detected in at least one of the following manners:

by detecting only a given energy range $\Delta\varepsilon^i$ of the total energy spectrum of said output radiation, where $\Delta\varepsilon^i$ depends on $E_i$; and by detecting only a given angular range $\Delta\theta^i$ of the total angular spectrum of said output radiation, where $\Delta\theta^i$ depends on $E_i$.

14. A method according to claim 2, wherein the series $\{E_i\}$ comprises a maximum landing energy $E_{max}$, and wherein:

the sample comprises biological tissue and $E_{max}$ is in a range of from 5 keV to 8 keV; or the sample is substantially non-biological and $E_{max}$ is in a range of from 30 keV to 60 keV.

15. A method according to claim 3, wherein the sample comprises biological tissue and $E_{max}$ is in a range of from 5 keV to 8 keV; or the sample is substantially non-biological and $E_{max}$ is in a range of from 30 keV to 60 keV.

16. A method according to claim 2, wherein $\Delta d$ is in a range of from 1 Mil to 1 nm.

17. A method according to claim 3, wherein $\Delta d$ is in a range of from 1 nm to 10 nm.

18. A method according to claim 1, wherein a series of scan images resulting from step (d) is not subjected to a mathematical deconvolution procedure.

19. A Charged Particle Microscope, comprising:

a specimen holder, for holding a specimen;

a source, for producing a probing beam of charged particles;

an illuminator, for directing said probing beam so as to irradiate the specimen;

a detector, for detecting a flux of output radiation emanating from the specimen in response to said irradiation; and a processor that is configured to:

(a) on a surface of the specimen, select a virtual sampling grid extending in an XY plane and having grid nodes to be impinged upon by said probing beam during a two-dimensional scan of said surface;

(b) select a landing energy $E_i$ for said probing beam, with an associated nominal Z penetration depth $d_i$ below said surface;

(c) at each of said grid nodes, irradiate the specimen with said probing beam and use said detector to detect output radiation emanating from the specimen in response thereto, thereby to generate a scan image $I_i$ of said surface, (d) repeat steps (b) and (c) for a series $\{E_i\}$ of different landing energies, corresponding to an associated series $\{d_i\}$ of different penetration depths;

(e) pre-select an initial energy increment $\Delta E_i$ by which $E_i$ is to be altered after a first iteration of steps (b) and (c);

(f) associate energy increment $\Delta E_i$ with a corresponding depth increment $\Delta d$ in the value of $d_i$;

(g) select said virtual sampling grid to have a substantially equal node pitch p in X and Y, which pitch p is matched to the value of $\Delta d$ so as to produce a substantially cubic sampling voxel; and (h) select subsequent energy values in the series $\{E_i\}$ so as to maintain a substantially constant depth increment $\Delta d$ between consecutive members of the series $\{d_i\}$.

20. A Charged Particle Microscope according to claim 19, wherein a series of scan images resulting from step (d) is not subjected to a mathematical deconvolution procedure.

* * * * *